United States Patent [19]

Fleenor

[11] Patent Number: 5,098,430
[45] Date of Patent: Mar. 24, 1992

[54] DUAL MODE ELECTROSURGICAL PENCIL

[75] Inventor: Richard P. Fleenor, Denver, Colo.

[73] Assignee: Beacon Laboratories, Inc., Broomfield, Colo.

[21] Appl. No.: 495,449

[22] Filed: Mar. 16, 1990

[51] Int. Cl.$^5$ .............................................. A61B 17/39
[52] U.S. Cl. ........................................ 606/42; 606/45; 606/49
[58] Field of Search ................. 606/41, 42, 45, 49, 606/22; 219/121.5, 121.51, 121.52

[56] References Cited

U.S. PATENT DOCUMENTS

| | | | |
|---|---|---|---|
| 2,618,267 | 11/1952 | Hanriot | 128/303.14 |
| 2,708,933 | 5/1955 | August | 128/303.14 |
| 2,828,747 | 4/1958 | August | 128/303.14 |
| 3,434,476 | 3/1969 | Shaw et al. | 606/22 |
| 3,562,486 | 2/1971 | Hatch et al. | 219/121.52 |
| 4,040,426 | 8/1977 | Morrison, Jr. | 128/303.17 |
| 4,060,088 | 11/1977 | Morrison, Jr. et al. | 219/121.51 |
| 4,562,838 | 1/1986 | Walker | 128/303.14 |
| 4,719,914 | 1/1988 | Johnson | 606/45 X |
| 4,781,175 | 11/1988 | McGreevy et al. | 128/303.17 |
| 4,901,719 | 2/1990 | Trenconsky et al. | 606/49 |
| 4,911,159 | 3/1990 | Johnson et al. | 606/45 X |

Primary Examiner—Lee S. Cohen
Attorney, Agent, or Firm—Sheridan, Ross & McIntosh

[57] ABSTRACT

A novel dual mode electrosurgical pencil is provided for conventional tissue cutting/coagulation use in a first mode of operation, and gas-enhanced coagulation by fulguration in a second mode of operation. The electrode and nozzle of the pencil are provided in a manner that permits relative positioning thereof, wherein the electrode extends sufficiently beyond the nozzle in the first mode for direct tissue contact, and is sufficiently nested within the nozzle in the second mode to accommodate laminar gas stream flow for effective gas-enhanced fulguration. In a preferred embodiment, a spring is utilized to maintain the nozzle in a retracted positiion during first mode use, and the pressure of an inert gas supply is utilized to move the nozzle from a retracted first mode position to a protracted second mode position. First and second mode control switches are provided on the gripping portion of the novel pencil in the preferred embodiment.

16 Claims, 2 Drawing Sheets

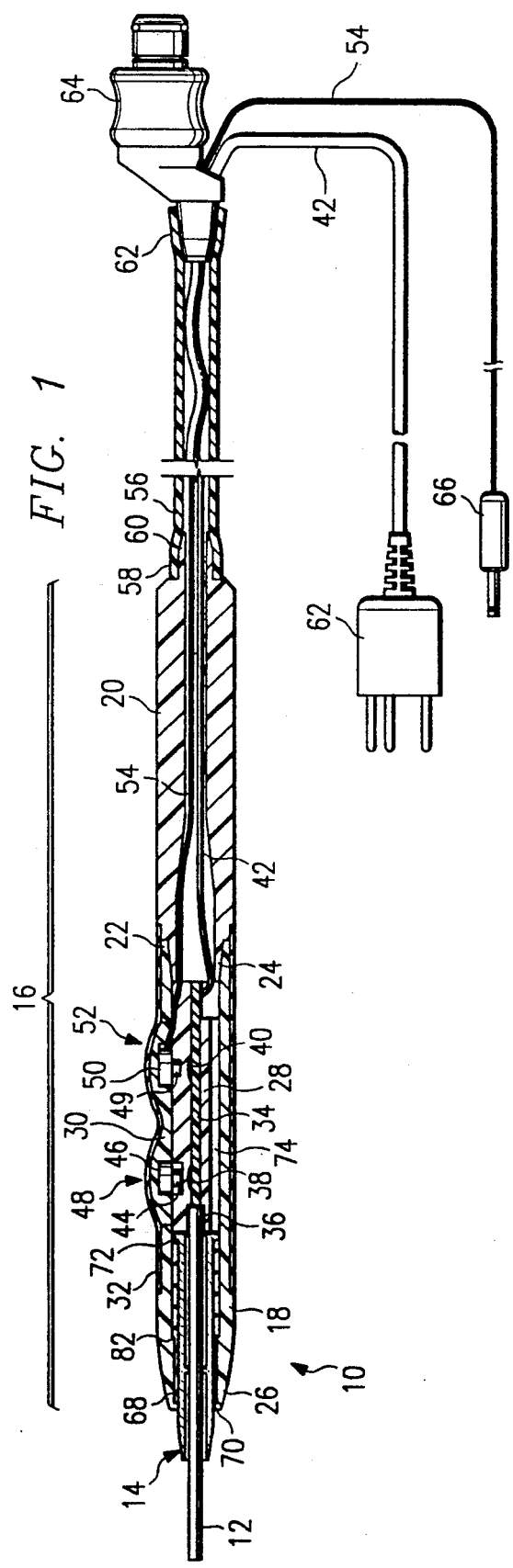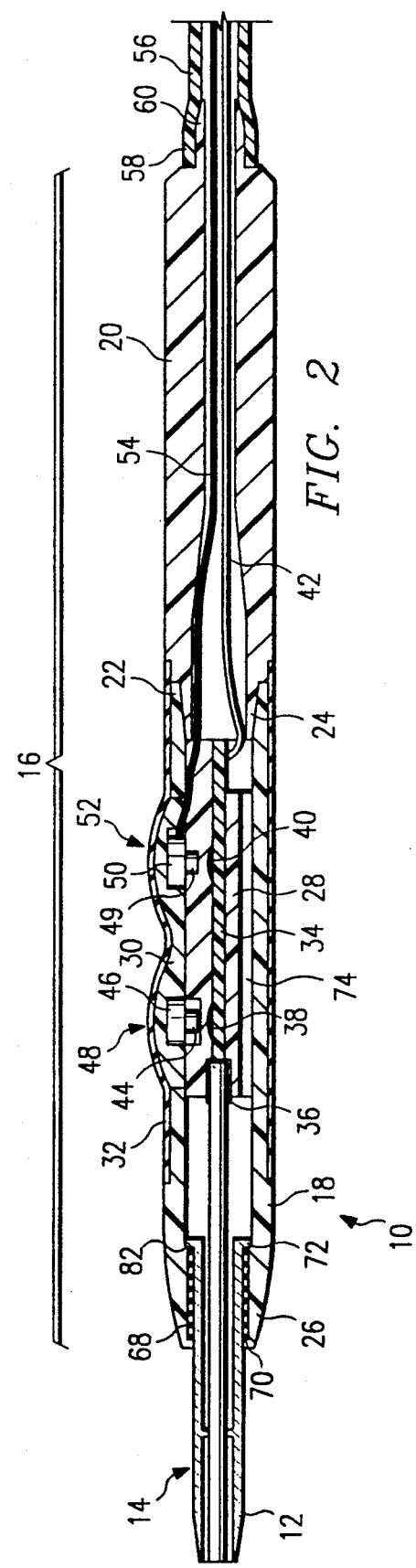

DUAL MODE ELECTROSURGICAL PENCIL

TECHNICAL FIELD OF INVENTION

This invention relates to electrosurgical devices, and in particular, to a novel dual mode electrosurgical pencil which can be selectively utilized for conventional tissue cutting and/or coagulation in a first mode of operation, and for gas-enhanced coagulation by fulguration in a second mode of operation.

BACKGROUND OF THE INVENTION

The use of electrosurgical pencils for tissue cutting and coagulation is well-known. In conventional electrosurgical pencils, an electrode is provided with an RF signal sufficient to cut or coagulate tissue when the electrode contacts and/or is positioned in close proximity to the tissue. Many of such early devices employed gas streams, or envelopes, about an electrode, believing the same would minimize any risk that the electrode discharge would ignite a surrounding explosive atmosphere. See, e.g. U.S. Pat. No. 2,618,267 to Hanriot, and U.S. Pat. Nos. 2,708,933 and 2,828,747 to August. Further, gas streams have been employed in electrosurgical pencils for purposes of initiating electrical discharge from an electrode, see U.S. Pat. No. 4,040,426 to Morrison, Jr., and to clear smoke from the surgical site, see U.S. Pat. No. 4,562,880 to Walker.

Most recently, it has been realized that a properly controlled inert gas stream surrounding an electrode can enhance tissue coagulation by evenly delivering charge to the tissue via ionized inert gas particles. See, e.g. U.S. Pat. No. 4,781,175 to McGreevy et al. Coagulation in this manner is advantageously achieved without direct electrode/tissue contact, and can be generally referred to as gas-enhanced fulguration. To effectively practice this technique, it is necessary to provide a nozzle about an electrode to achieve an acceptably laminar inert gas flow. Stationary positioning of a nozzle for such purposes, however, effectively precludes use of the corresponding electrode for conventional tissue cutting and/or coagulation by direct contact.

As such, and in view of the fact that no known electrosurgical pencil comprises an electrode and complimentary nozzle that can assume different relative positions, it is currently necessary for a surgeon to employ two separate pencils if both conventional direct contact procedures and gas-enhanced, non-contact fulguration procedures are to be carried out, as is increasingly desirable. Relative to a single pencil, the utilization of two separation pencils, and possibly two separate interfacing support systems, entails time-consuming, double-handling during surgery, additional space requirements in the surgical area, and a greater investment in surgical equipment.

SUMMARY OF THE INVENTION

Accordingly, a primary objective of the present invention is to provide a dual-mode electrosurgical pencil that can be selectively employed for conventional direct contact tissue cutting/coagulation in a first mode of operation, and for gas-enhanced, non-contact fulguration in a second mode of operation.

A further objective of the present invention is to provide an electrosurgical pencil wherein an electrode and nozzle are relatively and selectively positionable in an efficient manner, such that the electrode can be sufficiently exposed for conventional first-mode operation and sufficiently nested within the nozzle for second-mode gas-enhanced fulguration operation.

An additional objective of the present invention is to provide an electrosurgical pencil wherein the nozzle will automatically move from a first mode retracted position, relative to the electrode, to a second mode protracted position upon the delivery of inert gas to the pencil.

Another objective of the present invention is to provide a dual mode electrosurgical pencil that permits first and/or second mode selection via control means conveniently provided on the pencil.

Yet a further objective of the present invention is to provide a disposable dual mode electrosurgical pencil which accommodates efficient dual-mode use while minimizing material and assembly requirements.

Additional objectives and corresponding advantages will be apparent to those skilled in the art.

The present invention satisfies the desired objectives by disposing a nozzle and electrode for relative movement therebetween and incorporating means to achieve selective, relative positioning. In the preferred embodiment such positioning is achieved by slidably mounting a nozzle within one end of a pencil housing for movement relative to a stationary electrode. Further, a resilient means is positioned between the housing and nozzle and the preferred embodiment to maintain the nozzle in a first-mode retractive position sufficient to permit direct electrode/tissue contact for conventional cutting and coagulation procedures.

A gas delivery means is provided for delivering an inert gas to the nozzle, and in the preferred embodiment such means includes at least one internal passageway within a hand-held portion of the pencil. The nozzle and passageway(s) are provided so that, upon the delivery of an inert gas stream, the pressure thereof will bear against a portion of the nozzle, overcome the force of the resilient means and cause the nozzle to automatically and slidably assume a more forward position sufficient to achieve acceptable laminar flow of the inert gas for second-mode gas-enhanced fulguration.

Power and gas control means are preferably included for controlling the provision of an RF signal and inert gas stream to the pencil for cutting and coagulation operations in both the first and second modes. In the preferred embodiment, such means include pressure switches disposed on the hand-held portion of the pencil for convenient, selective control by a user. A gas delivery means and power control means, as well as the positioning means, gas delivery means and additional components further described hereinbelow are implemented in the preferred embodiment to accommodate effective and efficient use in assembly, as will be appreciated by those skilled in the art.

DESCRIPTION OF THE DRAWINGS

FIG. 1 is a cross-sectional side view of the preferred embodiment of the present invention in a first mode of operation, wherein the electrode and nozzle are positioned for conventional direct contact tissue cutting and/or coagulation; and, FIG. 2 is a cross-sectional side view of the preferred embodiment of the present invention in a second mode of operation, wherein the electrode and nozzle are positioned for gas-enhanced tissue coagulation by fulguration.

DETAILED DESCRIPTION OF PREFERRED EMBODIMENT

Figure 3:
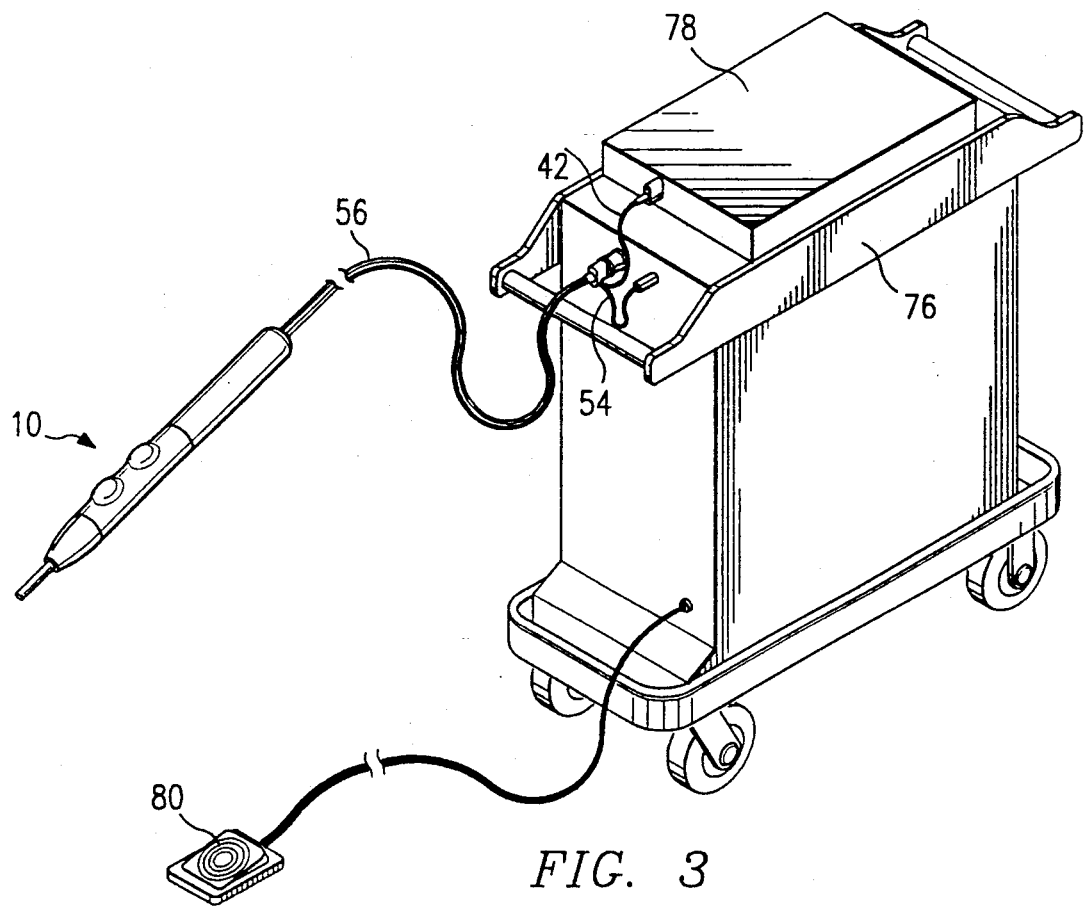
FIG. 3 shows the preferred embodiment of the present invention interconnected for dual mode operations with an inert gas supply means and electrosurgical generator.

FIGS. 1 and 2 show a preferred embodiment of the novel dual-mode electrosurgical pencil 10, wherein a conventional electrode 12 is exposed for conventional first-mode operation (FIG. 1), and wherein electrode 12 is in a nested position relative to nozzle 14 for gas-enhanced second-mode operation (FIG. 2).

The outer configuration of the hand-held portion 16 of the pencil 10 is principally defined by cylindrical, hollow nose housing 18 and cylindrical, hollow tail housing 20, which include nose housing collar 22 and tail housing collar 24, respectively, for concentric, opposing adjoinment. The nose and tail housings 18 and 20 may be of molded plastic construction and contoured for optimal handling by a user. For example, and as shown in FIG. 1, a forward portion 26 of nose housing 18 can be tapered inward to optimize finger control and work-site observation by a user during surgical procedures.

In the preferred embodiment, a boot assembly comprising inner boot 28, intermediate boot 30 and sheath-like outer boot 32 extends through nose housing 18, and supports, orients, insulates and protects components for selective control of first and second mode operations of the pencil 10. By way of example, the interior of nose housing 18 and exterior of inner boot 28 can be matingly contoured and/or otherwise adapted for interconnection (not shown). Inner boot 28 and intermediate boot 30 can be fabricated from a resilient elastomer and polyurethane. The outer boot 32 can also be fabricated from such materials, wherein the outer boot 32 will stretch upon assembly to retainingly engage nose housing 18, intermediate boot 30 and tail housing 20, and will enhance the grip and control of pencil 10 by a user.

Figure 4:
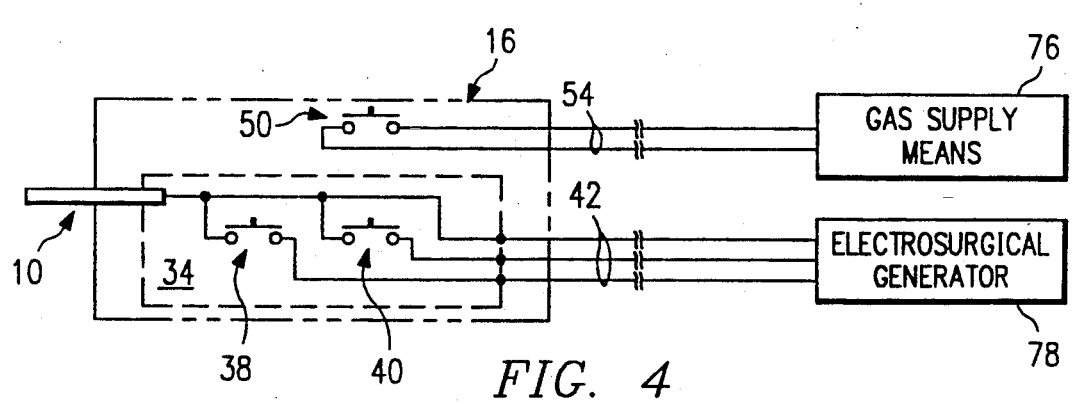
FIG. 4 is an electric schematic of the present invention interconnected for dual mode operations with an inert gas supply means and electrosurgical generator.

Inner boot 28 protectively supports an electric circuit board 34 and electrically interconnected socket 36, and socket 36, in turn, supports and electrically interconnects with electrode 12. As shown in FIGS. 1, 2 and 4, circuit board 34 is provided with first and second pressure snap dome switches 38 and 40, and is electrically interconnected to a three-conductor RF signal supply wire 42. Correspondingly, inner boot 28 and intermediate boot 30 support a first button 44 and button spacer 46 in an opposing relationship to the first snap dome switch 38, such that upon application of a predetermined pressure (e.g. 200 grams) by a user to a complimentary first bulge region 48 of outer and intermediate boots 32 and 30, the first snap dome switch 38 will be closed to initiate the provision of an appropriate RF signal to the electrode 10 for conventional, first-mode tissue cutting procedures.

Similarly, inner boot 28 and intermediate boot 30, support a second button 49 and pressure switch 50, respectively, in an opposing relationship to the second snap dome switch 40, such that upon application of a predetermined pressure (e.g. 200 grams) by a user to a complimentary second bulge region 52 of outer and inner boots 32 and 30, second snap dome switch 40 will be closed to initiate the provision of an appropriate RF signal to electrode 10 for first or second mode coagulation procedures. Pressure switch 50 is interconnected to a two-conductor gas supply signal wire 54, such that, upon the application of a predetermined pressure by a user to the second bulge region 52 (e.g. 300 grams), delivery of an inert gas to pencil 10 will be initiated for second mode gas-enhanced fulguration procedures. It should be appreciated that, in order to yield selective control over convenient first and second mode coagulation operations of the preferred embodiment, the amount of applied pressure necessary to initiate the provision of an RF signal for coagulation should be less than the amount of applied pressure necessary to initiate inert gas flow. Relatedly, in the preferred embodiment, the first bulge region 48 and second bulge region 52 of the outer boot 32 can be color coded consistent with existing electrosurgical generator power indicators (e.g. yellow and blue, respectively), to visually assist a user in proper and efficient employment of the pencil 10.

A gas supply hose 56 is connected at one end 58 to a nipple 60 of tail housing 18. The other end 62 of gas delivery hose 56 is connected to junction member 64, designed to interface with an inert gas supply means 76, as will be further discussed. The RF signal supply wire 42 and gas control signal wire 54 extend through the tail housing 20, gas supply hose 56, and exit from junction member 64. The RF signal supply wire 42 terminates in a standard plug 62 for interconnection with a standard electrosurgical generator 78. Similarly, gas supply signal wire 54 terminates in a two conductor plug 66 for interconnection with the inert gas supply means 76.

Of particular importance, nozzle 14 is slidably positioned within the nose housing 18 about electrode 10. A resilient spring member 68 is provided about nozzle 14 and is contained at a forward end by inner shoulder 70 of nose housing 18 and at a rearward end by nozzle flange 72, such that spring member 68 urges nozzle 14 to assume a sufficiently retracted position relative to electrode 10 for conventional, direct contact cutting/coagulation procedures. More particularly, and as will be appreciated by those skilled in the art, pencil 10 should preferably be designed so that electrode 12 projects approximately one-half inch or more from nozzle 14 for first-mode operation.

As shown in FIG. 1, the tail housing 20, nose housing 18 and boot assembly (i.e., 28 and 30) are constructed and interconnected to define inner passageway(s) 74 for the delivery of inert gas from gas supply hose 56 to the nozzle 14 during gas-enhanced second mode operations. In turn, the nozzle flange 72 is designed to interface with the inner passageway(s) 74 such that upon the supply of an inert gas, the pressure thereof will bear against the nozzle flange 72 to overcome the resiliency of spring member 68 and force nozzle 14 to automatically slide into a more protracted position limited by inner shoulder 82 of nose housing 18, as shown in FIG. 2, whereby the inert gas will be directed through nozzle 14 to achieve a sufficiently laminar flow for second-mode operations. More particularly, and as will be appreciated by those skilled in the art, pencil 10 should preferably be designed so that electrode 12 projects no more than approximately one-quarter inch, if at all, from nozzle 14 for effective second-mode gas-enhanced fulguration.

As noted above, and shown in FIG. 3, junction member 64 and conductor plug 66 of gas control signal wire 54 are interconnected with a gas supply means 76 for use of pencil 10. Such gas supply means may be a "BEAMER ONE" electrosurgical cart recently introduced by Beacon Laboratories, Inc. of Denver, Colo., U.S.A., or any other arrangement comprising an inert gas reservoir (e.g. tank) and an interconnected control means therefor (e.g. electronically actuated control valve), as will be appreciated by those skilled in the art.

Relatedly, standard plug 62 of RF signal supply wire 42 is interconnected with a standard electrosurgical generator 78 for use with pencil 10. By way of example only, electrosurgical generator 78 may be any of the following or equivalents thereof: the "FORCE 2" or "FORCE 4" generators of Vallylab, Inc.; the "EMS 4400" or "EMS 5000" of Bard Electro Medical Systems, Inc.; or the "EXCALIBER" of Aspen Laboratories, Inc. These products are designed to receive standard plug 62, and can be preset to selectively provide an appropriate first predetermined RF signal (e.g. 1 to 300 watts) for tissue cutting and an appropriate second predetermined RF signal (e.g. 1 to 120 watts) for coagulation.

To initiate conventional first mode tissue cutting, first bulge operation 48 is pressed by the user (e.g. with 200 grams of pressure) to initiate the provision of the preset cut signal from electrosurgical generator 78, through RF signal supply wire 42 and circuit board 34 to electrode 12. The release of pressure from first bulge portion 48 will, of course, terminate the cut signal. When conventional first mode coagulation procedures are to be initiated, second bulge portion 52 is pressed by the user (e.g. with 200 grams of pressure) to initiate the provision of the preset RF coagulation signal from electrosurgical generator 78, through RF signal supply wire 42 and circuit board 34 to electrode 12. To automatically initiate second mode gas-enhanced fulguration, the user simply presses second bulge portion 52 harder (e.g. with at least 300 grams of pressure), thereby closing switch 50 such that gas supply signal wire 54 provides a signal to the gas supply means 76 to initiate the supply of inert gas through supply hose 56 and passageway(s) 74 of the pencil 10, to the nozzle 12.

As will be appreciated upon consideration, the preferred embodiment is readily disposable, and is designed to minimize material and assembly requirements. In the latter regard, the spring 68, nozzle 14, inner boot 28 and interconnected components (e.g. circuit board 34 and electrode 12) can be readily end-loaded into nose housing 18; the intermediate boot 30 and components supported thereby can be side-loaded into nose housing 18 and retainingly engaged by outer boot 32; and tail housing 20 can thereafter be interconnected to nose housing 18.

While the present invention has been described in relation to a specific preferred embodiment comprising numerous beneficial features, numerous alternative embodiments are believed to fall within the broad scope of the invention. For example, and without limitation, while the preferred embodiment most practically provides for the movement of a nozzle relative to a stationary electrode, alternative embodiments could provide for the movement of an electrode relative to a stationary nozzle. Relatedly, while the preferred embodiment conveniently utilizes the pressure of an inert gas supply to automatically achieve relative electrode/nozzle positioning, alternative embodiments could employ mechanical or other positioning means (e.g. a slidable member for physical movement of a nozzle or electrode into the desired position).

Further, and without limitation, while the preferred embodiment conveniently provides first and second mode control switches directly on the gripping portion of a pencil, such switches could be separately provided. For example, the gas supply switch 50 of the preferred embodiment could be separately provided at a third bulge location (not shown) on the pencil 10 and/or totally separate via a foot switch 80 connected to the gas supply means 76, as shown in FIG. 3. Similarly, a 2-wire switch for selectively initiating tissue cutting and/or coagulation could be separately provided in a foot switch connected to a gas supply means 76.

Additional alternative embodiments apparent to those skilled in the art in view of the foregoing are intended to be within the scope of the present invention as further defined by the claims set forth below.

What is claimed is:

1. An electrosurgical pencil, comprising:
    an elongated housing, an electrode and a nozzle having a common longitudinal axis and being interconnected to said housing for relative axial movement between said electrode and nozzle along said axis, said nozzle being located about at least a portion of said electrode, positioning means interconnected to said housing and operatively associated with at least one of said nozzle and said electrode for axially positioning said electrode and said nozzle relative to each other in a first relative positioning for a first, non-gas enhanced mode of operation and a second relative position for a second, gas enhanced mode of operation, wherein the nozzle is more forward relative to the electrode in said second relative position than in said first relative position; and
    gas delivery means for forward delivery of an inert gas past said electrode during said second mode of operation for gas enhanced electrosurgery.

2. An electrosurgical pencil as recited in claim 1, wherein said gas delivery means comprises:
    at least one passageway within said housing for delivering gas to said nozzle.

3. An electrosurgical pencil as recited in claim 1, wherein said positioning means responds to the pressure of the gas to cause said relative positioning of the electrode and the nozzle during said second mode of operation.

4. An electrosurgical pencil as recited in claim 3, wherein the nozzle is slidably provided within the housing to permit movement of the nozzle relative to the electrode and said housing.

5. An electrosurgical pencil as recited in claim 1, further comprising:
    power supply control means for selectively controlling the supply of at least a first RF signal to said electrode from an interconnected electrosurgical generator.

6. An electrosurgical pencil as recited in claim 5, wherein said power supply control means comprises a first control switch, wherein said first control switch is mounted on said housing to permit a user to selectively cause the supply of a predetermined first RF signal to said electrode.

7. An electrosurgical pencil as recited in claim 6, wherein said power supply control means comprises a second control switch mounted on said housing to permit a user to selectively cause the supply of a predetermined second RF signal to said electrode.

8. An electrosurgical pencil as recited in claim 1, further comprising:
   gas supply control means for selectively controlling the supply of gas to said nozzle from an interconnected gas supply.

9. An electrosurgical pencil as recited in claim 8, wherein said gas supply control means comprises a control switch mounted on said housing to permit a user to selectively cause the supply of gas to said nozzle.

10. The electrosurgical pencil as recited in claim 1, wherein said nozzle is stationary and said electrode is movable relative thereto.

11. The electrosurgical pencil as recited in claim 1, wherein said electrode is stationary and said nozzle is movable relative thereto.

12. An electrosurgical pencil, comprising:
   an elongated housing;
   an electrode and a nozzle having a common longitudinal axis and being interconnected to said housing for relative movement between said electrode and nozzle along said axis, said nozzle being located about at least a portion of said electrode; and
   positioning means interconnected to said housing for relative axial positioning of said electrode and said nozzle, wherein said electrode and said nozzle are positionable in a first relative position for a first mode of operation and a second relative position for a second mode of operation, and wherein said nozzle is more forward relative to said electrode in said second relative position than in said first relative position, said positioning means comprising resilient means for maintaining said relative positioning of said electrode and nozzle during said first mode of operation.

13. An electrosurgical pencil as recited in claim 12, wherein said resilient means comprises:
   a spring positioned within said housing to resiliently bear against said nozzle.

14. An electrosurgical pencil, comprising:
   an elongated housing;
   an electrode and a nozzle having a common longitudinal axis and being interconnected to said housing for relative movement between said electrode and nozzle along said axis, said nozzle being located about at least a portion of said electrode;
   positioning means interconnected to said housing for relative positioning of said electrode and said nozzle along said axis, wherein said electrode and said nozzle are positionable in a first relative position for a first mode of operation and a second relative position for a second mode of operation, and wherein the nozzle is more forward relative to the electrode in said second relative position than in said first relative position; and
   power supply control means for selectively controlling the supply of at least a first RF signal to said electrode from an interconnected electrosurgical generator, wherein said power supply control means comprises a first pressure switch; and
   gas supply control means, including a second pressure switch, for selectively controlling the supply of gas to said nozzle from an interconnected gas supply, wherein the first pressure switch and the second pressure switch are mounted on said housing to permit a user to selectively cause the supply of predetermined RF signal to said electrode by applying a first predetermined pressure to a predetermined location, and to permit a user to selectively cause the supply of gas to said nozzle by applying a second predetermined pressure to the same said predetermined location.

15. An electrosurgical pencil comprising:
   an elongated housing;
   an electrode having first and second ends, wherein the first end is supportably interconnected to the housing, and wherein said second end projects beyond said housing;
   a nozzle mounted between at least a portion of said housing and said electrode, said electrode and nozzle having a common longitudinal axis, wherein said nozzle is positionable in a first position relative to said electrode for a first mode of operation and a second position relative to said electrode for a second mode of operation, wherein the second position is more forward than the first position; and
   positioning means interconnected to said housing and operatively associated with at least one of said nozzle and said electrode for axially positioning said electrode and said nozzle relative to each other; and
   means for delivering a gas to said nozzle during said second mode of operation, wherein said positioning means responds to the pressure of the gas to cause said relative positioning of the electrode and the nozzle during said second mode of operation.

16. An electrosurgical pencil as recited in claim 15, wherein:
   said nozzle is slidably provided within said housing to permit movement of said nozzle relative to said electrode and said housing.

* * * * *